US007674250B2

(12) United States Patent
Freyman et al.

(10) Patent No.: US 7,674,250 B2
(45) Date of Patent: Mar. 9, 2010

(54) METHODS OF DELIVERING THERAPEUTIC AGENTS

(75) Inventors: Toby Freyman, Watertown, MA (US); Maria Palasis, Wellesley, MA (US); Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 637 days.

(21) Appl. No.: 10/211,384

(22) Filed: Aug. 5, 2002

(65) Prior Publication Data
US 2004/0022864 A1    Feb. 5, 2004

(51) Int. Cl.
*A61M 31/00* (2006.01)
*A61B 17/32* (2006.01)
(52) U.S. Cl. .................... 604/522; 606/167; 606/181
(58) Field of Classification Search .............. 604/522; 606/167, 181
See application file for complete search history.

(56) References Cited

U.S. PATENT DOCUMENTS 6,749,617 B1 *   6/2004   Palasis et al. ............... 606/181

OTHER PUBLICATIONS

Verma IM, Gene Therapy: Twenty-first century medicine, 2005, Annu. Rev. Biochem. vol. 74, pp. 711-738.*
Parekh-Olmedo H, Gene therapy progress and prospects: targeted gene repair, 2005, Gene Therapy, vol. 12, pp. 639-646.*
Concalves M, A concise peer into the background, initial thoughts, and practices of human gene therapy, 2005, BioEssays, vol. 27, pp. 506-517.*
Marshall DJ, Biocompatibility of cardiovascular gene delivery catheters with adenovirus vectors: an important determinant of the efficiency of cardiovascular gene transfer, 2000, Molecular Therapy, vol. 1, pp. 423-429.*
Ravikumar et al., Clinical evaluation of a side entry access port; a novel dual-lumen venous access device, 1990, J. Clinical Oncology, vol. 8, Abstract.*
Yan, Feng et al., "*Synthesis of a Lipid Conjugate of $SO_3Le^a$ and Its Enhancement on Liposomal Binding to Activated Platets*," Biconjugate Chem, vol. 16, pp. 90-95 (2005).
Thiagaranjan, Perumal et al., "*Binding of Annexin V/Placental Anticoagulant Protein I to Platelets*," The Journal of Biological Chemistry, vol. 265, No. 29, pp. 17420-17423 (Oct. 15, 1990).

Nishiya, Takako et al., "*Interaction of Platelets with Liposomes Containing Dodecapeptide Sequence from Fibrinogen*," Thromb Haemost, vol. 91, pp. 1158-1167 (2004).
Gupta, Anirban Sen et al., "*RGD-Modified Liposomes Targeted to Activated Platelets as a Potential Vascular Drug Delivery System*," Thromb Haemost, vol. 93, pp. 106-114 (2005).
High, Katherine A., "*The Leaks Stop Here: Platelets as Delivery Vehicles for Coagulation Factors*," The Journal of Clinical Investigation, vol. 116, ,No. 7, pp. 1840-1842 (Jul. 2006).
Al, Hua et al., "*Electrostatic Layer-by-Layer Nanoassembly on Biological Microtemplates: Platelets*," American Chemical Society, Biomacromolecules, vol. 3, pp. 560-554 (2002).
Shi, Qizhen et al., "*Factor VIII Ectopically Targeted to Platelets is Therapeutic in Hemophilia A with High-Titer Inhibitory Antibodies*," The Journal of Clinical Investigation, vol. 116, No. 7, pp. 1974-1981 (Jul. 2006).
Jung, Ronald E., et al., "*Platelet-Rich Plasma and Fibrin as Delivery Systems for Recombinant Human Bone Morphogenetic Protein-$_2$*," Clin. Oral Impl. Res. vol. 16, pp. 676-682 (2005).
Bucki, Robert et al., "*Involvement of Phosphatidylinositol 4,5-Bisphosphate in Phosphatidylserine Exposure in Platelets: Use of a Permanent Phosphoinositide-Binding Peptide*," Biochemistry, vol. 40, pp. 15752-15761 (Nov. 2001).
Okumura, Yukihisa, et al., "*Transfer of Membrane Proteins from Human Platelets to Liposomal Fraction by Interaction with Liposomes Containing an Artificial Boundary Lipid*," Biochimica et Biophysica Acta, vol. 1194, pp. 335-340 (1994).
Hughes, K., et al., *Reversible Electropermeabilisation of Human and Rat Blood Platelets: Evaluation of Morphological and Functional Integrity 'in Vitro' and 'in Vivo,'* Biochimica et Biophysica Acta, vol. 981, pp. 277-287 (1989).
Neblock, Donald S. et al., "*Conjugation and Evaluation of 7E3×P4B6, a Chemically Cross-Linked Bispecific F (ab')$_2$ Antibody Which Inhibits Platelet Aggregation and Localizes Tissue Plasminogen Activator to the Platelet Surface*," Bioconjugate Chem., vol. 3, pp. 126-131 (1992).
Crawford, N., et al., "*Targeting Platelets Containing Electro-encapsulated Iloprost to Balloon Injured Aorta in Rats*," Thrombosis and Haemostasis, vol. 73, No. 3, pp. 535-542 (Mar. 1995).

(Continued)

*Primary Examiner*—Peter Paras, Jr.
*Assistant Examiner*—David Montanari
(74) *Attorney, Agent, or Firm*—Kenyon & Kenyon LLP

(57) ABSTRACT

Devices and methods of delivering therapeutic agents to tissue are provided, which provide reduced outflow of therapeutic agents from an injection site. The methods include delivering one or more clot-promoting substances, such as platelets, fibrin and/or thrombin, to the injection site to entrap the therapeutic agent in the injection site. Devices include devices that are suitable for use in the provided methods.

20 Claims, 3 Drawing Sheets

OTHER PUBLICATIONS

Hughes, Kenneth et al., "*Reversibly Electropermeabilized Platelets: Potential Use as Vehicles for Drug Delivery*," Biochemical Society, vol. 18, Part 5, pp. 871-873 (Oct. 1990).

El-Gamal, B.A.B., et al., "*Effect of Platelet Encapsulated Iloprost on Platelet Aggregation and Adhesion to Collagen and Injured Blood Vessels in Vitro*," Thrombosis and Haemostasis, vol. 68, No. 5, pp. 606-614 (1992).

Banning, Adrian, et al., "*Local Delivery of Platelets with Encapsulated Iloprost to Balloon Injured Pig Carotid Arteries: Effect on Platelet Deposition and Neointima Formation*," Thrombosis and Haemostasis, vol. 77, No. 1, pp. 1-225 (Jan. 1997).

Hughes, K. et al., *Reversible Electropermeabilisation of Human and Rat Blood Platelets: Evaluation of Morphological and Functional Integrity 'in Vitro' and 'in Vivo,'* Biochimica et Biophysica Acta, vol. 981, pp. 277-287 (1989).

\* cited by examiner

METHODS OF DELIVERING THERAPEUTIC AGENTS

FIELD OF THE INVENTION

The present invention relates to delivery devices and methods that provide reduced leakage and/or controlled release of therapeutic agents from an injection site resulting in increased agent uptake. According to embodiments of the present invention, methods are provided that include delivering one or more therapeutic agents and at least one clot-promoting substance to tissue. The clot-promoting substance preferably at least includes platelets.

BACKGROUND OF THE INVENTION

The treatment of disease such as vascular disease by local pharmacotherapy presents a means of delivering therapeutic drug doses to target tissues while minimizing systemic side effects. Such localized delivery of therapeutic agents has been proposed or achieved using medical devices such as catheters, needle devices and various coated implantable devices such as stents.

The localized delivery of therapeutic agents using needle devices has the advantages of precise placement and accurate control over the volume and rate of delivery. However, delivery using needle devices creates a needle track, which allows leakage or outflow of the therapeutic agent. Additionally, the nature of the tissue may allow for dispersion away from the injection site, which may not be desired.

SUMMARY OF THE INVENTION

The present invention includes methods of delivering one or more therapeutic agents to tissue, which include delivering the therapeutic agent and at least one clot-promoting substance to tissue. The clot-promoting substance preferably at least includes platelets. According to preferred embodiments of the invention, the therapeutic agent is delivered to tissue within modified platelets. Clot-promoting substances other than platelets and/or one or more extracellular matrix components such as collagen and/or elastin and the like, may be delivered to the tissue in accordance with the present invention, in addition to, or in lieu of platelets.

The invention further includes delivery devices that include means for delivering to tissue one or more therapeutic agents and at least one clot-promoting substance. Preferably the delivery devices of the present invention include a device that is capable of separating platelets from whole or partially processed blood. Also provided are delivery devices comprising at least one injection needle that is at least partially coated with at least one anti-clotting substance. The present invention further includes devices adapted to mix platelets and therapeutic agent in predetermined portions to form a mixture and an injection system adapted to inject the mixture into tissue.

DETAILED DESCRIPTION

Figure 1:
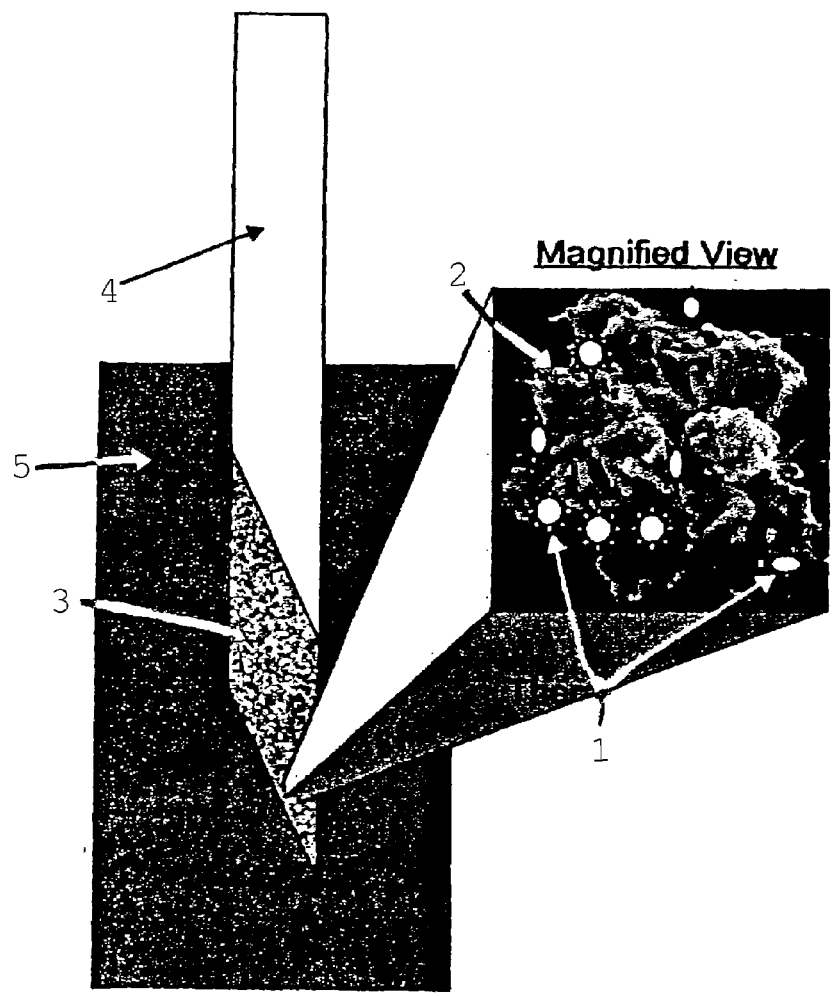
FIG. 1 depicts a magnified view of platelets and therapeutic agent delivered to tissue by a needle of a needle injection device (not shown) according to embodiments of the present invention.

When therapeutic agent is delivered to target tissue with an injection device such as a needle, leaking and dispersion often result upon removal of the device from the tissue. For example, a needle track is often formed in tissue after a therapeutic agent has been injected into a tissue with an injection device and subsequently removed from the tissue. Therefore, where an injection is performed via a needle, there is potential for leakage of the administered therapeutic agent along the needle track left by needle withdrawal.

This problem is exacerbated in situations where the therapeutic agent is injected into the tissue of an organ that undergoes expansion and contraction, such as the heart, in which muscular contractions actively pump the therapeutic agent out of the tissue track. In such cases, the organ wall thins during organ expansion, thus facilitating the leakage of previously-injected therapeutic agent from the organ tissue through the needle track and thereby decreasing the actual dose of therapeutic agent delivered to the target site and increasing systemic distribution of the drug. Thus, the efficiency of endocardial injection devices, for example, to deliver therapeutic agents to treat heart disease, in particular, is limited by poor retention of the therapeutic agent within tissue. As an example of the problem, it is estimated that less than 50% of radiolabeled protein delivered through endocardial injections is retained.

The present invention decreases the potential leakage of therapeutic agent by providing methods of delivering a therapeutic agent to tissue, which inhibits loss of an injected therapeutic agent prior to cell uptake. These methods include delivering one or more clot-promoting substance and one or more therapeutic agents to tissue.

The clot-promoting substances of the present invention include one or more substances that would promote clotting in mammals, known to those in the art. Preferably, the clot-promoting substances include platelets. However, other clot-promoting substances may be used in addition to, or in lieu of, platelets. For example, clot-promoting substances that may be used in accordance with the present invention include fibrinogen, fibrin, thrombin, and the like and combinations thereof The process by which the body prevents blood loss is coagulation. Coagulation involves the formation of a blood clot (thrombus) that prevents further blood loss from damaged tissue, blood vessels or organs. This process includes a cellular system including cells called platelets that circulate in the blood and serve to form a platelet plug over damaged cells and a second system based on the actions of multiple proteins (called clotting factors) that act in concert to produce a fibrin clot. These two systems work in concert to form a clot; disorders in either system can yield disorders that cause either too much or too little clotting.

When a break in a blood vessel occurs, substances are exposed that normally are not in direct contact with the blood flow. These substances (primarily collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding. The protein based system (the coagulation cascade) serves to stabilize the clot that has formed and further seal up the wound.

Platelets serve four primary functions (1) sticking to the injured blood vessel (platelet adherence), (2) releasing chemicals which attract and activate additional platelets, (3) attaching to other platelets to enlarge the forming plug (platelet aggregation), and (4) providing support (molecules on the surface of platelets are required for many of the reactions) for the processes of a coagulation cascade.

Platelets that may be used in accordance with the present invention may be platelets from a mammal (such as autologous platelets) and/or artificial platelets. Platelets from a mammal are preferably platelets from the specific mammal to be treated, that is, the mammal whose tissue is to be injected with therapeutic agent.

Autologous platelets may be obtained by methods known to those skilled in the art. According to embodiments of the present invention, Autologous Platelet Rich Plasma (Platelet Gel) is obtained and is delivered to the tissue to be treated. Platelet Gel was developed as a by-product of multicomponent pheresis. Methods of making Platelet Gel are known to those skilled in the art. A procedure may now be used, which utilizes the patient's own (autologous) platelets. An exemplary method of obtaining Platelet Gel is as follows: One unit of whole blood (approximately 450 milliliters) is drawn, either pre-operatively or in the operating room, into a standard blood collection bag containing a citrate-phosphate-dextrose anticoagulant. Alternatively, less blood may be used (e.g., as little as 50 milliliters of blood) to produce Platelet Gel. The blood is then centrifuged by using, for example, a variable-speed centrifuge autotransfusion machine or portable machine, to separate the buffy coat suspended in plasma from the red blood cell pack and platelet-poor plasma fraction. This is, the platelet concentrate used for Platelet Gel. Depending on the initial platelet counts, it is common to achieve platelet counts in excess of over three to five times baseline counts. Other factors that may be considered in quality of Platelet Gel include, for example, platelet viability and percent retained in the procedure. While white cell content increases 125% with selection for lymphocytes and monocytes, the inclusion of platelets and white cells appears to have several beneficial aspects. For example, white cells confer additional healing cytokines while providing antibacterial activity. On activiation with thrombin/calcium to form a coagulum, the platelets interdigitate with the forming fibrin web, developing a gel with adhesiveness and strength materially greater than the plasma alone. Thrombin/calcium also causes platelets to immediately release highly active vasoconstrictors, including beta thromboxane, serotonin and PDGF.

Upon injection into tissue, the platelets (or other clot-promoting substance) come into contact with matrix proteins (such as collagen), and soluble regulators released by other activated platelets or damage tissue, causing the platelets to activate and attach. In response to soluble regulators released by activated platelets (such as ADP and thromboxane A2), other platelets activate and attach resulting in a clot or a plug. Blood (for example, from a well vascularized myocardium in the case of heart tissue) may provide the other components necessary to form the clot (such as fibrin). Such components may be injected with the therapeutic agent or platelets to supplement or replace any components not received from blood. Natural processes result in resorption of the clot over time. The therapeutic agent is released in situ. The agent is released for example through migration (in the case of the therapeutic agent being cells) or diffusion (when the therapeutic agent is genes or drugs) or during resorption of the platelet plug, clot or coagulum.

According to embodiments of the invention, the method may further include adding, removing and/or delivering a substance that regulates the calcium ions present at the site of injection. Many of the attachments that platelets form require calcium ions. Therefore, their regulation may aid in enabling control over the plug or clot formation. Examples of substances capable of regulating calcium ions at an injection site include one or more of the following: integrins, such as integrins IIb and IIIa, NCS-1/frequenin, calcium chloride, crystallins, parvalbumins, oncomoculins, calmodulins, and the like and combinations thereof. An example of methods of regulating calcium ions includes nonspecific attachment to glycosamino-glycans (such as heparan sulfate). A further example includes the delivery in a dual lumen of platelets and alginate in one lumen and calcium in a second lumen. When delivered a two-fold plug formation occurs, 1) $Ca^{2+}$ and alginate and 2) $Ca^{2+}$ and platelets.

According to other embodiments, the methods further include delivering a protein to which platelets adhere (such as collagen). The combination of platelets and protein in these embodiments form an in situ, self cell seeding, tissue engineering scaffold. The type and amount of protein are selected so as to preferably form a porous network of protein and platelet that preferably provides a substrate suitable to encourage and substantially sustain cell migration, proliferation and function.

The methods of the present invention may optionally include delivering substances that activate platelets, such as thromboxane A2, ADP, or prostacyclins to the tissue. The delivery may be via a substance that is injected such as platelets, other clot-promoting substance, or the therapeutic agent or the delivery may be independent from other substances that are delivered. These substances that activate platelets can be injected for instance, substantially simultaneously with the platelets, other clot-promoting substance and/or the therapeutic agent through another lumen in the injection device or they can be released through some mechanism (such as by controlled release polymers) at the time of injection.

Therapeutic agents of the present invention are preferably delivered within artificial platelets. In these embodiments, small particles (such as polymeric particles or beads), which contain the therapeutic agent, attach to damaged tissue (such a collagen) and platelets or other clot-promoting substances, such as fibrin and/or thrombin, therefore becoming part of the clot. See for example, FIG. 2. In preferred embodiments, the particles interact with each other and damaged tissue in a manner similar to platelets. That is, once activated by attachment to damaged tissue or blood, the particles attach to one another.

According to these embodiments, artificial platelets preferably interact with blood and damaged tissue to form a plug within the needle track. The artificial platelets then release the therapeutic agent through one or more transport processes (such as, diffusion, degradation, osmotic pressure, and the like). These artificial platelets are preferrably delivered to the myocardium or other tissue by injection.

According to preferred embodiments the artificial platelets are biocompatible polymers with a modified surface. Surface modifications of the artificial platelets and/or particles to which they bind, preferably result in the attachment of the particles to the damaged tissue and to platelets. This attachment can be accomplished through a number of methods including the following:

(1) Conjugating molecules on the surface of the particles to which platelets will bind (such as collagen). Platelets bind to the particles and the damaged tissue forming a composite, anchored plug;

(2) Conjugating attachment proteins (such as integrins IIb and IIIa) to the surface of the particles. This allows for specific biological interactions to occur preferentially to others. The addition of a third material to which both platelets and particles may preferably attach may be necessary or desirable; or (3) Conjugating molecules (such as fibronectin, vitronectin, and the like) onto the particle's surface, which attach directly to platelets and/or to one or more extracellular matrix components to which platelets also attach (such as collagen). The particles, platelets, and molecules on the particles surface are preferably injected simultaneously.

Figure 3:
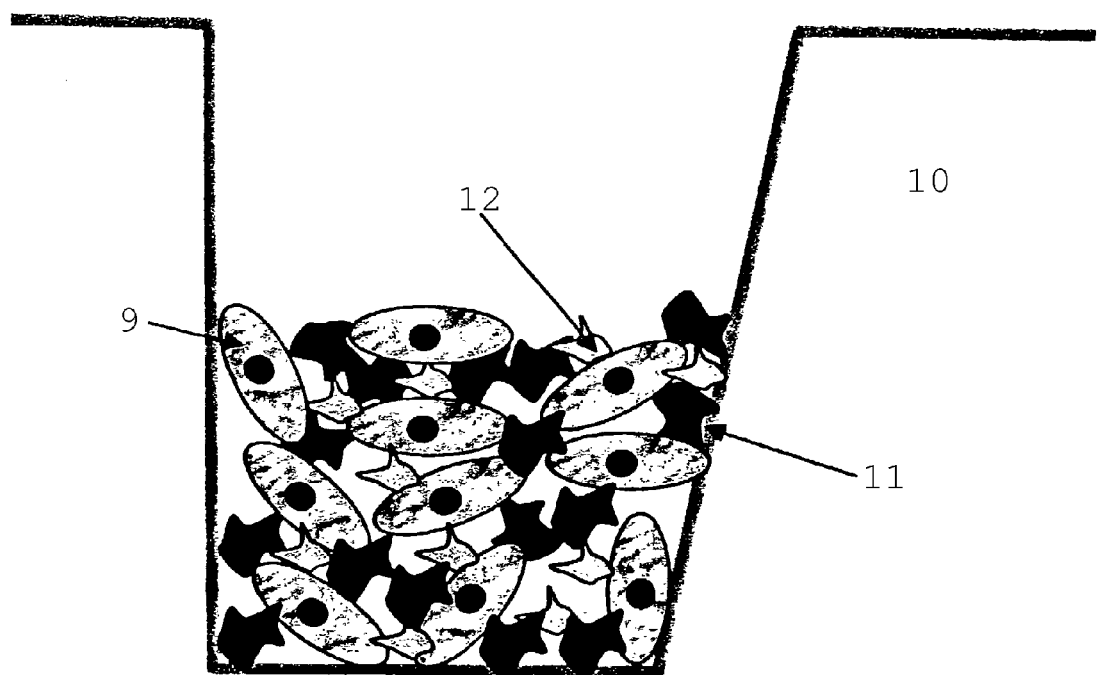
FIG. 3 depicts embodiments of the invention in which therapeutic agents, platelets and one or more extracellular matrix components, such as collagen and/or elastin has been injected into tissue.

Alternately, platelets or a third material such as fibronectin, vitronectin may be already present in the injection site (see for example FIG. 3). The particles may have integrins that attach to collagen binding domains. The particles may also have IIb and/or IIIa receptors to enhance platelet binding to the particles.

Modification of the particle's surface with extracellular matrix components (such as laminin, collagen and/or elastin or similar matrix proteins) may be accomplished by various methods. For example, such modifications may be as simple as a coating process. Methods of conjugation or coating of polymers with proteins are known to those skilled in the art, in particular with regard to preparation of cell culture plasticware and assays plates. Even partial or uneven coverage of the particle will allow for sufficient opportunity for interaction.

The artificial platelets are preferably formed from polymers or other biocompatible material (such as collagen, laminin, fibronectin, hyaluronic acid, and elastin), which contain the therapeutic agent in interstitial sites, pores or in a central cavity. Non-limiting examples of suitable polymers include for example, PLGA, PEG-PLGA, PCL, tryosine-derived polycarbonate, and polyanhydrides. The choice of particle material will depend for example on the therapeutic agent, but may also depend on other factors, such as the material's biocompatibility, degradation rate, and controlled release capabilities.

In certain embodiments of the present invention, both artificial platelets and autologous platelets are injected, such that the artificial platelets containing the therapeutic agent therein form a plug with autologous platelets. The attachment capabilities of artificial platelets with autologous platelets may assist in retaining therapeutic agent within the plug or clot, and thus, within the needle track.

According to preferred embodiments of the present invention therapeutic agents within polymeric particles having a modified surface are combined with the platelets prior to insertion into an injection device for injection into tissue or into space within the body such as an aneurysm. Alternatively, the therapeutic agent within such polymeric particles does not contact the platelets until during or after delivery to tissue, for example by delivery from a multi-lumen device.

According to other embodiments of the invention, loaded or modified platelets are used to deliver the therapeutic agent. According to these embodiments, loaded or modified platelets are used to deliver the therapeutic agent by carrying the therapeutic agent and releasing it within the injection site. This method is similar to transplantation of genetically modified cells, however, platelets do not have a nucleus or organelles for protein production. Because platelets do not have a nucleus, they cannot be genetically modified to produce therapeutic agents, like other cells. However, platelets contain numerous storage granules. Thus, the therapeutic agent may be incorporated into the platelet's storage granules. The granules may then be used to carry the therapeutic agent to an injection site.

Formation of storage granules with the therapeutic agent may occur during platelet formation or through in vitro manipulation of the platelets. Platelets are produced by megakaryocytes present in bone marrow. Genetic or other manipulation of megakaryocytes or their progenitors ex vivo will result in the production of platelets containing the therapeutic agent in its storage granules.

See for example, Blood Apr. 15, 1997; 89(8):2679-88. Another method that may result in platelets containing the therapeutic agent is in vitro platelet membrane permeabilization. This can be accomplished by several methods using for example, streptolysin O, dimethylsulfoxide, and electroporation.

A platelet modification technique that includes treating cells with streptolysin O (SLO) causes pores to be formed in the cell surface membrane, which are large enough to allow oligonucleotides to diffuse from the extracellular fluid into the cells cytoplasm. Such pores must be closed by the addition of fetal calf serum to the incubation media. Using this procedure some cells will be irreversibly permeabilized while others will remain unpermeabilized.

Thus, modification of platelets in accordance with these embodiments, may be made for example, by altering the platelet forming cells (megakaryocytes) or by in vitro manipulation of platelets to incorporate the therapeutic into the storage granules.

The type and amount of loaded, modified or artificial platelets may be selected depending on various factors such as the composition of the therapeutic agent, other materials being delivered, and the desired outcomes of using such platelets. For example, modified or artificial platelets provide for the dose of the therapeutic agent to be known. Their use also provides the therapeutic agent to be time released, with the release occurring, for example when the platelets degrade. See for example, Biol Blood Marrow Transplant 1999; 5(4): 215-21, in which platelets were produced that express nerve growth factor receptor.

According to preferred embodiments, platelets that have been modified to deliver and release therapeutic agent are delivered to the myocardium by injection. The platelets attach to damaged tissue in the needle track and form a plug. Once attached, the therapeutic agent releases by one or more of several methods, including for example, attachment stimulated therapeutic release (which is similar to the release of signaling factors from platelets upon attachment), platelet rupture (where platelets rupture in response to attachment or another stimulus), and/or breakdown of the platelet plug by macrophages and enzymes each of which is further described below.

Attachment stimulated therapeutic release is related to the changes platelets go through after attachment. Platelets go through many changes once attachment is made with specific ligands, including for example, increase in surface-to-volume ratio and a release of signaling factors. Given the many changes naturally occurring upon attachment, an attachment mediated release of therapeutic agent may occur.

Therapeutic agent may also be released by rupture of the platelet. Modification of the platelet such that upon activation and attachment, or some time after, the platelet releases a substance from its storage vesicles, which causes rupture.

Additionally, platelets naturally break down within a few days. Therefore, as the platelets are broken down the therapeutic agent will be released.

The present invention further includes methods that include delivering clot-promoting substances, such as fibrinogen, fibrin, thrombin, certain growth factors, gene vectors, cells, and the like and combinations thereof, with or in lieu of, platelets. As platelets are delivered to tissue they interact with blood components responding naturally to form a clot. The addition of other clot-promoting substances accelerates this process and therefore entraps the therapeutic before it can escape or be ejected from the needle track. Clot promoting substances according to the present invention may be any substance that enduces clot formation. The delivery of one or more of these substances with therapeutic agent, with or in lieu of platelets, preferably results in improved retention of therapeutic agents through clotting.

The delivery of multiple clotting substances and/or platelets may be accomplished using single or multi-lumen delivery devices, preferably injection devices, which deliver the substances, platelets or therapeutic agents in any combination of spatial or temporal configurations. For example, according to certain embodiments, platelets may be delivered to the tissue substantially simultaneously with the therapeutic agent, by use of an injection device that has multiple lumens where the platelets are delivered in one lumen and therapeutic agent in another. Alternatively, they may be delivered together in a single lumen. According to other embodiments, platelets are delivered substantially simultaneously with the therapeutic agent and other clot-promoting substances, such as fibrin or fibrinogen, through one or more same or different lumens of an injection device. According to other embodiments, therapeutic agent is delivered with thrombin for example, from a first lumen followed by delivery of platelets from a second lumen. According to these embodiments the therapeutic agent is preferably delivered distal to the platelets preferably resulting in the formation of a platelet plug, which traps therapeutic agent in the needle track. Other embodiments of the invention may result in entrapment of the therapeutic agent within the plug.

Clot-promoting substances other than platelets, such as fibrinogen, fibrin and thrombin and the like, are available commercially. According to embodiments of the present invention, clot-promoting substances are mixed with therapeutic agent before delivery or they are delivered substantially simultaneously with, before or after the therapeutic agent. For example, the clot-promoting substance may include multiple substances that form fibrin glue. In these embodiments, fibrin glue may be delivered in two parts, thrombin and fibrinogen, which form a fibrin mesh upon mixing. In preferred embodiments, the therapeutic agent is mixed with thrombin and injected substantially simultaneously (preferably via a dual lumen device) with fibrinogen.

Other clot-forming substances include combinations of substances such as calcium and alginate, which polymerize in situ to form a plug.

With regard to fibrin glues, a number of companies have developed kits called fibrin glues or sealants. The basic principle behind these kits is the same. Human thrombin and human fibrinogen are applied separately to a bleeding site, and this results in the instant formation of a thin film of fibrin which controls the bleeding. The substances are typically applied in a sterilized kit resembling such as a double-barrelled syringe or gun to facilitate surgical application, and the individual components are sprayed on. The film should not be swabbed away during surgery to maintain efficacy. The fibrin film gradually becomes completely resorbed, with no resulting fibrosis at the site. The human plasma is screened according to usual methods in the production process, but the individual components are subjected to virucidal treatments just as with conventional coagulation factor concentrates. Heat-treatment and solvent/detergent treatment are used by different manufacturers.

Efficacy may be enhanced by inclusion of other substances in the glue or sealant, which promote stability of the fibrin film. Accordingly, the present methods may further include delivering stability-promoting substances that would be known to those skilled in the art, such as tranexamic acid, aprotinin or factor XIII, and the like. Available products include for example Beriplast (Centeon) and Fibrin Sealant produced by the Scottish National Blood Transfusion Service in Edinburgh.

Fibrin glues are generally only for topical use. However, adverse systemic effects have not been reported after application to internal bleeding surgical sites. The glues may be of use for instance, in treatment of some haemophilic bleeding episodes. However, they may also be used to control bleeding in non-haemophilic patients undergoing other surgeries, such as hip or knee replacement surgery, to the extent that the patients do not require a blood transfusion.

According to other embodiments of the invention, fibers or fibrous substances may be delivered to tissue independently or incorporated into a substance being injected into tissue, e.g., platelets, other clot-promoting substances, and/or therapeutic agent, to reinforce the plug that forms. Preferably the fibers or fibrous substances are relatively inert.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, adenoassociated virus, retrovirus, lentivirus and a-virus), polymers, hyaluronic acid, tissues, gene therapies, proteins, cells and the like, or combinations thereof, with or without targeting sequences. The injection administered in accordance with the invention includes the therapeutic agent(s) and solutions thereof.

Specific examples of therapeutic agents used in conjunction with the present invention include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Some examples of the applicable cells include slide population cells, lineage negative cells, Lin-CD34$^-$, Lin-CD34$^+$, Lin-cKit$^+$, mesenchymal stem cells, cord blood cells, cardiac or other tissue derived stem cells, whole bone marrow, BM-MNCs (bone marrow mononuclear cells), EPCs (endothelial progenitor cells), skeletal myoblasts, muscle derived cells, Go cells, endothelial cells, adult cardiomyocytes, fibroblasts, smooth muscle cells, MSC$_s$+5-aza, adult cardiac fibroblastsl+5-aza, genetically modified cells, tissue engineered grafts, MyoD scar fibroblasts, pacing cells, embryonic stem cell clones, embryonic stem cells, fetal or neonatal cells, immunologically masked cells, tissue engineered grafts, genetically modified cells, and teratoma derived cells.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Tissues to which therapeutic agents may be delivered by the methods of the present invention or using the injection devices of the present method include any mammalian, preferably human, tissue (or organ or space), whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke, aneurism or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

Therapeutic agents may be directly injected into tissue, or may be delivered in a solution or other form and may be delivered via a carrier. Therapeutic agents may be delivered for example via microspheres that are injected into the tissue, rather than injecting therapeutic agents directly into the tissue. In embodiments of the invention, therapeutic agents may be injected via microspheres into muscle tissue. Injecting therapeutic agents via microspheres may result in sustained release or delivery of the drug.

According to embodiments of the invention, therapeutic cells for delivery as the therapeutic agent may be modified according to embodiments of the present invention such that specific adhesion proteins are expressed on their surface, which promote clumping or clotting in the presence or absence of platelets. Modifications may be accomplished by genetically modifying the cells to express the proteins on the cell surface or through conjugating the adhesion proteins onto the receptors already expressed on the cell's surface.

According to other embodiments, drugs or genes as the therapeutic agent may be modified such that it will bind to platelets or other components in the clot. These embodiments include modification of the drug or gene without substantially negatively affecting its ability to function. An example of such a modification includes modifying a region of a gene that adheres so strongly to the platelets or other components that it separates from the therapeutic portion upon interaction with cells and other substances within the body. Alternately, the link between the modified region and the therapeutic portion could be cleaved by an enzyme common to healing wounds (such as, collagenase).

Therapeutic agents of the present invention may be injected in an amount determined by those skilled in the art depending on various factors, including for example, the tissue being injected, the type of agent being injected, the mode of injection, carrier or solution, the clot-promoting substance being delivered, and the severity of the condition being treated.

When the therapeutic agent includes cells for example, if the therapeutic agent is delivered in a suspension of platelets, the suspension may be too viscous to deliver efficiently or accurately. Accordingly, the type of clot-promoting substance and/or the amount or type of therapeutic agent may need to be adjusted to attain a desirable viscosity. Accordingly, the amount of cells being delivered may be reduced as compared to previous quantities of cells, without detrimental effect, given the increased efficiency of the present methods, such that the viscosity is at an appropriate level.

In preferred embodiments, therapeutic agents are delivered to muscle tissue by injecting a therapeutic agent directly into the muscle tissue. In more preferred embodiments, the muscle tissue is heart tissue, even more preferably, heart tissue of a human. Direct injection of therapeutic agents may represent an effective means to treat the entire myocardium. Injected agents tend to disperse throughout the myocardium into uninjected areas. Thus, the number of injections that is necessary in order to deliver therapeutic agents to a specific area of tissue may be decreased.

According to preferred embodiments, the methods of the present invention include methods of delivering a therapeutic agent to a tissue of a mammal in need of the therapeutic agent, including injecting at least one therapeutic agent and injecting one or more clot-promoting substances into tissue of a mammal. Preferably, the mammal is a human.

Delivery of materials, agents and other substances according to the present invention may be accomplished by use of an injection device. The injection device may be any injection device known to those skilled in the art, including for example injection devices having an injection needle. Examples of specific devices incorporating injection needles, and thus within the scope of the invention, include needle injection catheters, catheters, hypodermic needles, biopsy needles, ablation catheters, cannulas and any other type of medically useful needle. It will be understood by one of ordinary skill in the art that other injection devices are contemplated and are within the scope of the invention. Specifically, any device competent to penetrate or separate tissue is contemplated, particularly those that create an opening through which a delivered agent may escape or "leak out," including for example, a lumen in the device with walls that are shaped such that it can penetrate or separate tissue. A non-limiting example of such a device is an Infiltrator™ balloon catheter. Non-needle injection devices are also contemplated by the present invention. Examples of non-needle injection devices include, but are not limited to, transmural myocardial revascularization (TMR) devices and percutaneous myocardial revascularization (PMR) devices or any other device capable of wounding or creating a channel or crater in tissue. Further examples of suitable injection devices include ablation devices and needle-free injectors which propel fluid using a spring or pressurized gas, such as carbon dioxide injection devices.

The delivery devices of the present invention preferably include means for delivering to tissue one or more therapeutic agents and at least one clot-promoting substance, such as the means described herein.

According to embodiments of the present invention, the injection device, which may include an injection needle is at least partially coated to prevent the clot from sticking or reduce sticking to the needle or other injection device and potentially being disturbed during needle removal. The coating may include any anti-clotting material known in the art that would have the effect of reducing a clot sticking to it. Non-limiting examples of such coatings include for example heparin, hydrogels, teflon and silicone. The present invention includes delivery devices include at least one injection needle that is at least partially coated with at least one anti-clotting substance.

The injection device may contain one or more lumens depending on various factors including for example whether the clot-promoting substances are combined with therapeutic agent before, during or at the time of injection, and on whether any other substances are being delivered. When clot-promoting substances are combined with therapeutic agent at the time of injection, the clot-promoting substance may be delivered after, before, or substantially concurrently with injection of the therapeutic agent. Additional lumens may be added for other purposes. According to embodiments of the invention, the clot-promoting substance is combined with the therapeutic agent before delivery, and the injection device includes only one lumen. If additional substances are to be injected however, additional lumens may be included in the injection device depending on what substance is being injected and whether it is desirable to keep the additional substance separate from the therapeutic agent for whatever reason. According to other embodiments, the clot-promoting substance is not combined with the therapeutic agent until after delivery of the therapeutic agent and the clot-promoting substance. The injection device of these embodiments, preferably has at least two lumens so the therapeutic agent and clot-promoting substance may be delivered separately. Additional lumens may be present in these embodiments as well.

The present invention includes devices adapted to mix platelets and therapeutic agent in predetermined portions to form a mixture and an injection system adapted to inject the mixture into tissue.

In embodiments of the injection device having more than one lumen, the spatial relationship of the lumens with respect to each other may be varied. According to embodiments having at least two lumens, the first lumen may be within the second lumen or adjacent to the second lumen.

Additionally, the depth and deployment of each lumen into tissue is controlled together or independently from one another. Preferably, the depth and deployment of each lumen is controlled independently from one another. Such a device having independently controlled lumens is preferably controlled manually or by some control device, such that one may determine which lumen to deploy first, how far into the tissue or away from the tissue the therapeutic agent or second substance should be injected, and the timing of each injection, such as whether to deploy the lumens and inject their contents substantially simultaneously or how soon after one deployment, the other lumen is deployed. The order, depth and timing of deployment should be determined by those skilled in the art depending on various factors such as the composition of the therapeutic agents (and/or their carriers), the clot-promoting substances (including consideration of their physical characteristics, such as their relative viscosities and miscibility with each other) or any other substance being injected or delivered to the tissue, and the tissue being injected.

In embodiments where the therapeutic agent and the clot-promoting substance are delivered separately, the clot promoting substance may be injected in substantially the same location of the tissue as the therapeutic agent, before, concurrently with, or after injection of the therapeutic agent. For example, the clot-promoting substance may be delivered into a needle track formed in tissue injection of the therapeutic agent, such that when a clot forms, the clot blocks therapeutic agent from escaping the needle track. This delivery may include any form of injection via needle or non-needle methods.

The delivery device optionally includes a system within it or working with it to separate platelets. The system may include a device adapted to separate platelets from whole or partially processed blood by filtration. The delivery device of the present invention may integrate a filtration system into a handle or long portion (such as a catheter) of the delivery device. The system of these embodiments preferably separates platelets from larger blood components (such as, blood cells) by using a filter (preferably about a 4 micron filter) to allow platelets and plasma to pass through the filter. Plasma is then preferably removed, to concentrate the platelets, by methods known in the art, such as by using another filter (preferably a less than 1 micron filter) or by using an osmotic or diffusive process.

Another method of separating platelets according to these embodiments, is by platelet specific binding. According to this method, beads or surfaces are used that specifically bind platelets as whole or partial blood passes over them. The bound platelets are then released by a releasing agent or degradation of the beads, surface or binding molecule. The platelets are then concentrated by filtration and/or an osmotic or diffusive process. The delivery devices of the present invention preferably include devices that are capable of separating platelets from whole or partially processed blood.

FIG. 1 shows a magnified view of therapeutic agent 1 and platelets 2 delivered to an injection site in tissue 5 by a needle 4 of an injection device, according to methods of the present invention. According to the depicted embodiments, therapeutic agent and platelets are delivered substantially simultaneously to the tissue and a clot 3 is formed within the tissue, which entraps much of the therapeutic agent and reduces outflow of the therapeutic agent after the needle is withdrawn. Preferably the platelets 2 are autologous platelets, that when injected with the therapeutic agent 1, form a platelet plug or clot 3 within the needle track. This plug attaches to the tissue of the needle track and traps the therapeutic agent, thus improving retention of the agent.

Figure 2:
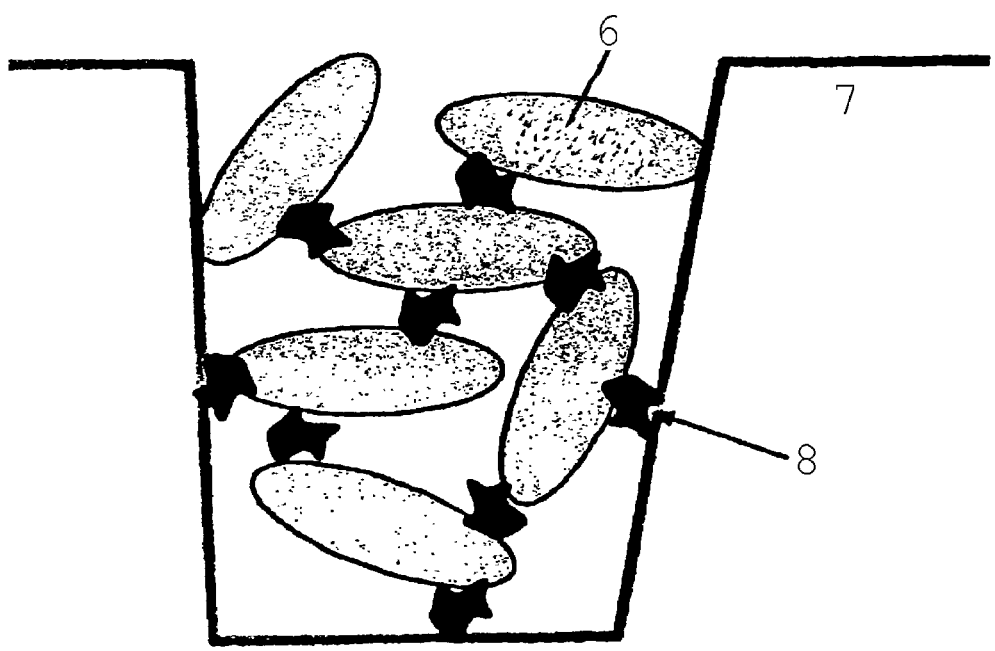
FIG. 2 depicts platelets and therapeutic agent within a needle track of myocardium after having been delivered to myocardium tissue by methods of the present invention.

FIG. 2 depicts artificial platelets 6 that contain the therapeutic agent therein and form a plug with platelets 8 from blood after being injected into mycardium or other tissue 7 according to methods of the present invention. According to these embodiments, small particles are constructed to attach and aggregate, in situ, in a manner similar to platelets (artificial platelets). For example, polymer beads may act as such artificial platelets, in that they may contain the therapeutic agent, attach to damaged tissue (e.g., collagen) and attach to platelets.

FIG. 3 shows improved retention of therapeutic agents in tissue 10, such as myocardium tissue, by adhesive interaction between therapeutic agents 9, platelets 11 and a third material 12 of extracellular matrix components, such as collagen and/or elastin. In the embodiments depicted in FIG. 3, the therapeutic agents 9 are preferably modified so they will adhere both to platelets 11 and the collagen 12. The collagen 12 may serve one or more purposes. For example, it may serve to fill space and create a more solid plug and/or it may have some therapeutic value. The collagen may also serve as a substrate for new cells, to bind the therapeutic for longer release profiles, or to bind endogenous growth factors to mediate the wound healing response.

According to preferred embodiments of the present invention, platelets are preferably platelets from the patient to whom the therapeutic agent will be delivered. Various methods of obtaining platelets may be used. According to a suitable method, a blood sample is collected (preferably from the patient to be injected) before the procedure during which the therapeutic agent will be injected. Platelets are separated from the blood sample using standard hematological techniques. Slight modifications to standard methods of isolation and preparation of platelets may be required to obtain the desired purity and concentrations of platelets, so as to improve injectate delivery. For example, the isolation process or portions thereof, may be repeated to achieve platelets having greater purity. Preferably, the platelets are purer than $5 \times 10^6$ white blood cells for $4 \times 10^{11}$ platelets. The concentration of platelets is preferably more than 2 million platelets per µL.

In a case in which cells are the therapeutic agent, the platelets are preferably prepared such that a plug of the platelets can provide sufficient attachment sites on which the cells can migrate, function and proliferate.

According to these embodiments of the invention, platelets and cells may be isolated substantially simultaneously during an apheresis procedure. The apheresis procedure can be tailored to yield the therapeutic cells and platelets at a desired concentration. The cells and platelets may then be mixed outside the delivery device and delivered together. Alternatively, the cells and platelets may be mixed in the correct proportion within the delivery device. Thus, delivery devices according to the present invention may include those adapted to deliver platelets and therapeutic cells isolated during an apheresis procedure. The device optionally mixes these components in the desired predetermined proportions and delivers them directly to the tissue to be injected, preferably the myocardium. According to these embodiments, preferably one or more additional substances are mixed with the platelets and cells for various beneficial reasons, such as to enhance the therapeutic effect (e.g., growth factor) or to improve retention (e.g., collagen and/or elastin).

Platelets or other clot-promoting substances may prematurely attach or aggregate in response to signals in a suspension in which they are carried or on injection device surfaces. Accordingly, one or more anti-clotting agents and/or coatings of contact surfaces may be added to the platelets (or other clot-promoting substances) or injection devices to prevent clotting during collection, storage and delivery of the platelets. The injection device surfaces can be passivated by coating surfaces of the device that will come into contact with the clot-promoting substance, with heparin or similar compounds (STS Biopolymers Inc.) Aggregation due to signals in the suspension of platelets may be passivated by the addition of anticoagulation factors, such as heparin or other anticoagulation factors.

By way of example, less than 100 microliters of anticoagulation factor may be ultimately delivered to the tissue along with the clot-promoting substance. This small volume of anticoagulation factor should not be sufficient to necessarily prevent clotting in the tissue. Rather, the relatively large volume of the surrounding tissue should dilute and neutralize the anticoagulant quickly enough so as to allow the clot to form before needle removal.

According to particularly preferred embodiments of the present invention, platelets are combined with a therapeutic agent to be delivered to the patient. They are added directly to the therapeutic agent before the therapeutic agent is inserted into an injection device. Alternatively, the platelets are mixed with the therapeutic agent during the delivery process, for example, mixed in the injection device itself, such as in the handle, or mixed upon release of the therapeutic agent and clot-promoting substance from the injection device if each is carried through the device in separate lumens of the device.

According to these embodiments, the platelets and/or other clot-promoting substance(s) and the therapeutic agent are then injected into the myocardium. Preferably the injection is relatively slow, that is, from about 10 to about 60 seconds, depending on the amount and type of substance being injected. The needle may optionally be maintained in the tissue after injection for an additional time period to further prevent leakage. For example, according to certain embodiments of the invention the needle remains in contact with tissue for about an additional 10-60 seconds after injection.

During and after injection, the platelets or other clot-promoting substance(s) become activated as they contact damaged tissue, for example, and being to form a platelet plug or clot. Damaged tissue may include for example, tissue damaged by formation of a needle track from the injection or tissue damaged by any other cause. Any anti-coagulant present will be quickly diluted due to the small volume of injectate (e.g., about 50 to about 200 µl, or preferably about 100 µl) compared to the volume of the surrounding tissue. Blood present (from for example, injury to a highly vascularized myocardium), may provide other clotting components and signals necessary to form a relatively stable clot.

Injectate according to the present invention, whether it includes therapeutic agent, platelets or other clot-promoting substances or any combination thereof, may be modified in accordance with the present invention as it passes out of the distal end of the delivery device, preferably out of the distal end of the needle injection catheter. Preferably, such modifications include chemical, electrical, mechanical and/or biological modifications that aid in clotting after the injectate is injected into tissue. Chemical modifications in accordance with these embodiments include for example, removing heparin from the injectate by passing it over heparin binding beads or surfaces before exiting the needle. An example of an electrical modification includes ionizing certain molecules by applying an electric field, radiation or radio frequency to induce the clotting or clumping reaction. Mechanical modifications include increased pressure or shear stress induced molecular changes or chemical reactions resulting in the initiation of a clotting or clumping phenomenon. An example of a biological modification in accordance with the present invention includes adding or removing a growth factor (such as PDGF) or other signaling molecule within the distal portion of the device. Removal may be accomplished for example by selective binding on a surface or the surface of the beads.

A plug or clot forms from the clot-promoting substance. Preferably, the plug or clot forms relatively rapidly. When the clot-promoting substance includes platelets, the clot forms due to soluble signaling factors released by activated platelets and the small wound volume.

Retention of the therapeutic agent is preferably increased due to the clot forming around it. In addition, once activated, platelets may attach directly to the agent due to adhesion molecules on the platelet's surface. For example, surface receptors become active and bind to their ligands or surface becomes charged and therefore, interacts with other charged surfaces. Over time, the clot is resorbed and the therapeutic agent released. The therapeutic agent may also diffuse (as in the case of drug or gene agents) or migrate (as in the case of cell agents) into the surrounding tissue.

The present invention will now be described in detail with respect to showing how certain specific representative embodiments of the methods of the present invention, the apparatus components and process steps being understood as examples that are intended to be illustrative only. In particular, the invention is not intended to be limited to the physical orientation of injection device components, order of the steps and the like specifically recited herein.

EXAMPLE 1

A blood sample is collected from a patient before a procedure is performed during which therapeutic agent is injected into a tissue of the patient. Platelets are separated from the blood sample using standard hematological techniques. An anti-clotting agent is added to the platelets to prevent clotting during collection, storage and delivery of the platelets. The platelets are combined with a therapeutic agent to be delivered to the patient.

The platelets and therapeutic agent are then slowly injected into the myocardium over about 10 to about 60 seconds using a needle injection device. The needle injection device is maintained in contact with tissue for about an additional 10-60 seconds after injection. During this time the platelets become activated due to contact with damaged tissue (for example, from a needle track formed by the injection), and begin to form a platelet plug or clot. Blood present from injury to a highly vascularized myocardium, provides other clotting components and signals necessary to form a stable clot.

The platelet plug forms relatively rapidly due to soluble signaling factors released by activated platelets and the small wound volume. Retention of the therapeutic agent is increased due to the clot forming around it. Over time, the clot is resorbed and the therapeutic agent released.

While the present invention is described with respect to particular examples and preferred embodiments, it is understood that the present invention is not limited to these examples and embodiments. In particular, the types of therapeutic agents and clot-promoting substances and the design of the injection device are not intended to be limited by the present examples.

Moreover, the present invention is not limited to the method steps recited herein and may contain additional steps, such as delivery of substances other than therapeutic agents and clot-promoting substances, deploying additional lumens, performing steps such as radiofrequency cautery or other steps that may reduce outflow, and/or adding additional ingredients to the therapeutic agent or clot-promoting substances, as would be apparent to those skilled in the art based on the present disclosure so as to reduce outflow of therapeutic agent from tissue. Additionally, the present invention is not limited to the sequence of the method steps.

The present invention as claimed therefore, includes variations from the particular examples and preferred embodiments described herein.

What is claimed is:

1. A method of delivering a therapeutic at a target site comprising:
    inserting a catheter into the body of a patient;

guiding an end of the catheter towards a tissue target site within the body of the patient;

creating a channel in the target site with the catheter;

delivering a therapeutic contained in the catheter to the target site;

delivering platelets contained in the catheter to the target site wherein there is incremental clotting of the platelets; and after delivering the therapeutic and platelets, removing the catheter from the target site, wherein the incremental clotting of the platelets prevents the leakage of the therapeutic from the target site after the catheter removal, and wherein the platelets are delivered before, substantially simultaneously with or after the delivery of the therapeutic, and wherein the therapeutic is not carried by the platelets.

2. The method of claim 1 wherein the platelets were previously taken from the patient.

3. The method of claim 1 further comprising:

premixing the platelets and therapeutic prior to inserting the catheter into the body of the patient.

4. The method of claim 1 wherein the catheter contains a coated piercing tip, the coating reducing the adherence between a clot formed in the target site and the piercing tip.

5. The method of claim 1 further comprising:

separating platelets out of a patient's blood with a filtration system in the catheter.

6. The method of claim 1 wherein creating a channel in the target site with the catheter comprises:

inserting a piercing tip into the target site;

retaining the piercing tip in the target site for a predetermined period of time;

and removing the piercing tip from the target site.

7. The method of claim 3, wherein the platelets were previously taken from the patient.

8. The method of claim 3, wherein the catheter contains a coated piercing tip, the coating reducing the adherence between a clot formed in the target site and the piercing tip.

9. The method of claim 3, further comprising separating platelets out of a patient's blood with a filtration system in the catheter.

10. The method of claim 3, wherein creating a channel in the target site with the catheter comprises:

inserting a piercing tip into the target site;

retaining the piercing tip in the target site for a predetermined period of time;

and removing the piercing tip from the target site.

11. The method of claim 1, further wherein the therapeutic is carried within a first lumen in the catheter and the platelets are carried within a second lumen in the catheter.

12. A method of delivering a therapeutic at a target site comprising:

inserting a catheter into the body of a patient;

guiding an end of the catheter towards a tissue target site within the body of the patient;

creating a channel in the target site with the catheter;

delivering a therapeutic contained in the catheter to the target site, wherein the therapeutic is carried by a plurality of platelets and wherein there is incremental clotting of the platelets; and after delivering the therapeutic, removing the catheter from the target site, wherein the incremental clotting of the platelets prevents the leakage of the therapeutic from the target site after the catheter removal.

13. The method of claim 12, wherein the platelets were previously taken from the patient.

14. The method of claim 12, wherein the therapeutic is released when the platelets rupture.

15. The method of claim 12, wherein the platelets are artificial.

16. The method of claim 12, wherein the catheter contains a coated piercing tip, the coating reducing the adherence between a clot formed in the target site and the piercing tip.

17. The method of claim 12, further comprising separating platelets out of a patient's blood with a filtration system in the catheter.

18. The method of claim 12, wherein creating a channel in the target site with the catheter comprises:

inserting a piercing tip into the target site;

retaining the piercing tip in the target site for a predetermined period of time;

and removing the piercing tip from the target site.

19. The method of claim 15, wherein the artificial platelets are polymer beads.

20. The method of claim 12, wherein the therapeutic is a pharmaceutically active compound, pharmaceutically active protein, pharmaceutically active polypeptide or pharmaceutically active liposome.

* * * * *